(12) United States Patent
Hata et al.

(10) Patent No.: US 6,558,920 B1
(45) Date of Patent: May 6, 2003

(54) HIGH EXPRESSION SYSTEM OF PROTEINS

(75) Inventors: Yoji Hata, Osaka-fu (JP); Hiroki Ishida, Kyoto-fu (JP); Hiromoto Hisada, Kyoto-fu (JP); Eiji Ichikawa, Kyoto-fu (JP); Akitsugu Kawato, Kyoto-fu (JP); Yasuhisa Abe, Kyoto-fu (JP); Koji Suginami, Kyoto-fu (JP); Satoshi Imayasu, Kyoto-fu (JP)

(73) Assignee: Gekkeikan Sake Company Limited (JP)

( * ) Notice: Subject to any disclaimer, the term of this patent is extended or adjusted under 35 U.S.C. 154(b) by 0 days.

(21) Appl. No.: 09/517,529

(22) Filed: Mar. 2, 2000

(30) Foreign Application Priority Data

Jun. 1, 1999 (JP) .............................. 11-154271
Feb. 15, 2000 (JP) ....................... 2000-036754

(51) Int. Cl.$^7$ .............................. C12N 9/34; C12N 9/26; C12N 1/14; C07H 21/04
(52) U.S. Cl. ................ 435/69.1; 435/320.1; 435/254.3; 435/205; 435/201; 536/23.2; 536/24.1
(58) Field of Search .......................... 435/252.3, 320.1, 435/440, 71.2, 254.3, 205, 69.1, 201; 536/23.1, 23.2, 24.1

(56) References Cited

FOREIGN PATENT DOCUMENTS

| JP | 7-51067 | 2/1995 |
|----|---------|--------|
| JP | 10-84968 | 4/1998 |

OTHER PUBLICATIONS

Davies et al. (1994) Prog Ind Microbiol 29:527–560.*
Tsuchiya et al. (1994) Biosci Biotechnol Biochem 58(5):895–899.*
Jefferson et al., "β–Glucuronidase from *Escherichia coli* as a gene–fusion maker", *Proc. Natl. Acad. Sci*, vol. 83, pp. 8447–8451, (1986).
Unkles et al., "The development of a homologous transformation system for *Aspergillus oryzae*, based on the nitrate assimilation pathway: A convenient and general selection system for filamentos fungal transformation", *MGG*, vol. 218, pp. 99–104, (1989).
Fujita et al., "Molecular cloning and nucleotide sequence of the protyrosinase gene melO, from *Aspergillus oryzae* and expression of gene in yeast cells", *BBA*, vol. 1261, pp. 151–154, (1995).

* cited by examiner

*Primary Examiner*—Rebecca E. Prouty
*Assistant Examiner*—David J. Steadman
(74) *Attorney, Agent, or Firm*—Browdy and Neimark, PLLC

(57) ABSTRACT

According to the protein expression system in which a variety of desired useful proteins are highly produced by fusing a coding region of useful protein gene to the downstream of a promoter region of a tyrosinase-encoding gene (melO) of *Aspergillus oryzae* by a usual method of DNA manipulation, transferring a plasmid containing the resulting novel fusion gene into *Aspergillus oryzae* and incubating the thus-obtained transformant, various proteins can efficiently be produced at a high purity and in a high yield.

10 Claims, 6 Drawing Sheets

FIG. 1

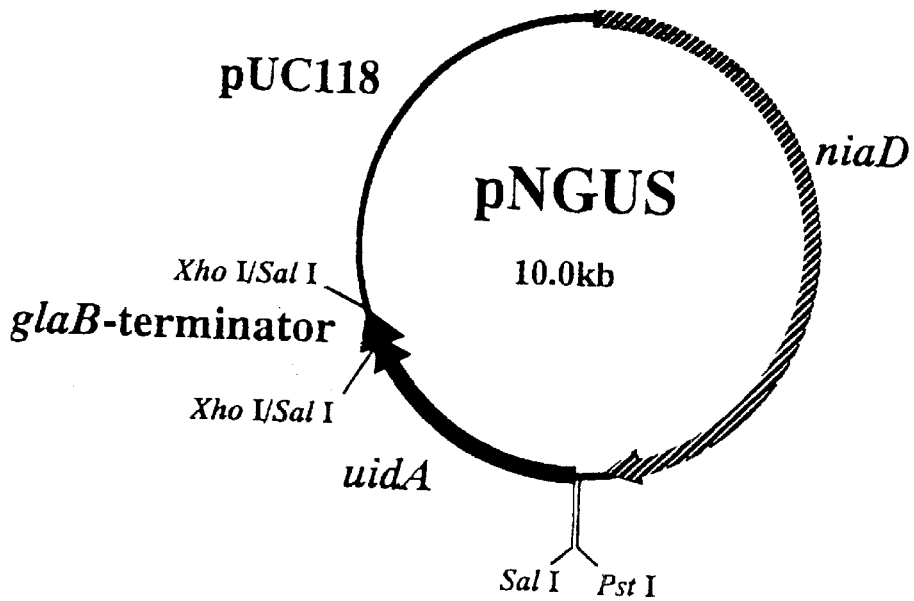

FIG. 2

-1173 gcttgccttggctcaaatcgttcatgacacccatctaggccatggcgcctgtag
agcaggttacatttcatggccggttaatccgaatccagtgcttgcacatgtagc
gccacatggtctgtgctattctattctgtgttataatagtgtgatttattgcgt
ttgggcgtttcagttgattcgactggccttgcacattactctcgcattccacag
ctggctggaggagttatctttacttcttctttgtgactgtggctgcatgaggcg
cttagtatactatcagctgatactatgttgaaactgaatcacggtgcttgaagg
tctgcgtgaagtggttcattgggctgtgatattaaccgcagcctgtctagaact
atgactagacggagcgccaagaatggacgacaacaggaatactgcccagctagc
cacagctgaatcctaaagaagtttgccagccctcgtattcctatcctgcatgga
cggcaacattgccctgacgagctaaattaggccgcagcgctagtattagaatga
actacggtagcaatgaggggaacgcccacaagccaattaaacgtccctttcttg
atatgacgggcctagccttaattacggggtactgtgaggacgttgtgcctgctg
caattgtctatccgtgccgacggtgttgacagccactagccattcagctcgcca
cactttcaaccccacacctcaaagtaagacctaaacttatttggacttccttg
cagctactatgctgtcactgttatttgactggacatgacatgcagtatcatggc
gccaataaagagagtatctcgagagtttcattgcatcgtaggaaaggcttgcat
tccggtgttgccgggaaagggatcattggtaatgcgtagttgttttgtctagct
gtgatgccgggctttgatggacggaggacctggagtgcagctcttcatgcaaag
cccgagatagactgatttgtaacatgtgtgatgcgtatcattcattatcaatac
gtctcgtggatatttaagaagggcgacagtcgtgtgaatatccgctacttcaag
ttcaaaacatcattcctacgaaaaggaaaaccacagcttccgcttcaaagccct
agtcaacactagttcatcttctgattactttggttcaca

```
              10         20         30         40         50         60
         gcttgccttg gctcaaatcg ttcatgacac ccatctaggc catggcgcct gtagagcagg
              70         80         90        100        110        120
         ttacatttca tggccggtta atccgaatcc agtgcttgca catgtagcgc cacatggtct
             130        140        150        160        170        180
         gtgctattct attctgtgtt ataatagtgt gatttattgc gtttgggcgt ttcagttgat
             190        200        210        220        230        240
         tcgactggcc ttgcacatta ctctcgcatt ccacagctgg ctggaggagt tatctttact
             250        260        270        280        290        300
         tcttctttgt gactgtggct gcatgaggcg cttagtatac tatcagctga tactatgttg
             310        320        330        340        350        360
         aaactgaatc acggtgcttg aaggtctgcg tgaagtggtt cattgggctg tgatattaac
             370        380        390        400        410        420
         cgcagcctgt ctagaactat gactagacgg agcgccaaga atggacgaca acaggaatac
             430        440        450        460        470        480
         tgcccagcta gccacagctg aatcctaaag aagtttgcca gccctcgtat tcctatcctg
             490        500        510        520        530        540
         catggacggc aacattgccc tgacgagcta aattaggccg cagcgctagt attagaatga
             550        560        570        580        590        600
         actacggtag caatgagggg aacgcccaca agccaattaa acgtcccttt cttgatatga
             610        620        630        640        650        660
         cgggcctagc cttaattacg gggtactgtg aggacgttgt gcctgctgca attgtctatc
             670        680        690        700        710        720
         cgtgccgacg gtgttgacag ccactagcca ttcagctcgc cacactttca accccacacc
             730        740        750        760        770        780
         tcaaagtaag acctaaactt attttggact tccttgcagc tactatgctg tcactgttat
             790        800        810        820        830        840
         ttgactggac atgacatgca gtatcatggc gccaataaag agagtatctc gagagtttca
             850        860        870        880        890        900
         ttgcatcgta ggaaaggctt gcattccggt gttgccggga aagggatcat tggtaatgcg
             910        920        930        940        950        960
         tagttgtttt gtctagctgt gatgccgggc tttgatggac ggaggacctg gagtgcagct
             970        980        990       1000       1010       1020
         cttcatgcaa agcccgagat agactgattt gtaacatgtg tgatgcgtat cattcattat
            1030       1040       1050       1060       1070       1080
         caatacgtct cgtggatatt taagaagggc gacagtcgtg tgaatatccg ctacttcaag
            1090       1100       1110       1120       1130       1140
         ttcaaaacat cattcctacg aaaaggaaaa ccacagcttc cgcttcaaag ccctagtcaa
            1150            melO promoter        1180       1190       1200
         cactagttca tcttctgatt actttggttc acaatgcgga acaaccttct ttttccctc
            1210       1220       1230            glaB cds   1250       1260
         aatgccattg ctggcgctgt cgcgcatccg tccttcccta tccataagag gcagtcggat
            1270       1280       1290       1300       1310       1320
         ctcaacgcct tcattgaggc acagacaccc atcgcaaac agggcgtcct caataatatc
            1330       1340       1350       1360       1370       1380
         ggcgctgatg gcaagcttgt tgaggggct gccgctggta tcgttgtagc ctccccatcc
            1390       1400       1410       1420       1430       1440
         aagagtaatc ccgactgttc gtacaatcct accctcaaga ccgcatgata ttaccacaga
            1450       1460       1470       1480       1490       1500
         gctaactata tatagacttc tacacctgga cgcgcgacgc tggcctcacc atggaagaag
            1510       1520       1530       1540       1550       1560
         tgatagagca attcatcggg ggagatgcga ctctcgagtc cacaatccag aattatgttg
``` melO PROMOTER REGION (1-1173)

melO PROMOTER REGION (1174-3093)

glaB TRANSLATION REGION

FIG. 4

```
            1570       1580       1590       1600       1610       1620
       actctcaagc gaacgagcag gcagtctcca acccatcagg cggcctgtcg gatggctcgg
            1630       1640       1650       1660       1670       1680
       gtcttgctga acccaaattt tacgtcaata tctctcaatt caccgattct tggggccgac
            1690       1700       1710       1720       1730       1740
       cccagcgcga cgggccagcc ttacgtgctt ccgctttgat cgcatatggc aactctctga
            1750       1760       1770       1780       1790       1800
       tttccagcga caaacaatct gttgtcaaag ctaacatctg gccaattgtc cagaatgact
            1810       1820       1830       1840       1850       1860
       tgtcttatgt gggtcaatac tggaaccaga ccgggtttga tctttgggaa gaggttcagg
            1870       1880       1890       1900       1910       1920
       gcagctcctt cttcactgtt gctgtgcagc acaaagcctt ggtggagggc gatgcgtttg
            1930       1940       1950       1960       1970       1980
       caaaggcact cggagaggaa tgccaggcat gctccgtggc gcctcaaatc ctctgccatc
            1990       2000       2010       2020       2030       2040
       ttcaggactt ctggaatggg tctgctgttc tttctaactt accaaccaat gggcgcagtg
            2050       2060       2070       2080       2090       2100
       gactggatac caactctctt ttgggctcca ttcacacttt tgatccagcc gccgcttgtg
            2110       2120       2130       2140       2150       2160
       atgatacaac attccagccc tgctcctctc gcgccctgtc gaaccataag cttgtggttg
            2170       2180       2190       2200       2210       2220
       actctttccg gtcggtctac ggtatcaaca atggacgtgg agcaggaaag gccgcggcag
            2230       2240       2250       2260       2270       2280
       tgggcccgta cgcagaggac acctatcagg gaggcaatcc atggttggta ctctgtctca
            2290       2300       2310       2320       2330       2340
       tatccaaagc ttaaactaat gaatattagg tatcttacca ccctggtcgc tgcggaattg
            2350       2360       2370       2380       2390       2400
       ctctacgacg ccttgtatca gtgggacaaa caaggtcaag tgaacgtcac tgaaacttcc
            2410       2420       2430       2440       2450       2460
       cttcccttct tcaaggacct ctccagcaat gtcaccaccg gatcctacgc caagtcttcc
            2470       2480       2490       2500       2510       2520
       tcagcctatg agtcgcttac gagcgctgtc aagacctacg cagacggctt catctccgtt
            2530       2540       2550       2560       2570       2580
       gtccaggagt atactcccga tggcggtgct ttggctgagc agtacagtcg ggaccagggc
            2590       2600       2610       2620       2630       2640
       accccagttt cggcatccga tctgacttgg tcttatgcag ctttcttgag tgctgttgga
            2650       2660       2670       2680       2690       2700
       cgacgaaacg gcactgtccc tgctagctgg ggctcttcca cggccaacgc agttccaagc
            2710       2720       2730       2740       2750       2760
       caatgttcgg ggggtacagt ttctggaagt tacactaccc caactgttgg gtcgtggtag
            2770       2780       2790       2800       2810       2820
       atgtactttc cagtgcgtgt agtctactct gacctcgtgt cacgattgtt gcttttgcct
            2830       2840       2850       2860       2870       2880
       gtctaaatgc gaccgtgctg tgcatgtttg ttaaatactg tcattcatct ttgtttcaac
            2890       2900       2910       2920       2930       2940
       aacaaagatt acatcaatta gtgctagcta gacaataact tttacagttg caacgttagt
            2950       2960       2970       2980       2990       3000
       cctagtatta tacatctcac cggatcctct tcaaacttca cggggtaacc aaaagaaagt
            3010       3020       3030       3040       3050       3060
       aacaagacta agcctattga tactgtggtt ctaatcttat tttagtttcc tgtacgtcca
            3070       3080       3090 3093
       ctgcaatcaa actaagtata catactacat cct
``` glaB TRANSLATION REGION (1174-3093)

SEQUENCE LISTING

```
<160> NUMBER OF SEQ ID NOS: 1

<210> SEQ ID NO 1
<211> LENGTH: 3093
<212> TYPE: DNA
<213> ORGANISM: Aspergillus oryzae

<400> SEQUENCE: 1
gcttgccttg gctcaaatcg ttcatgacac ccatctaggc catggcgcct gtagagcagg      60
ttacatttca tggccggtta atccgaatcc agtgcttgca catgtagcgc cacatggtct     120
gtgctattct attctgtgtt ataatagtgt gatttattgc gtttgggcgt ttcagttgat     180
tcgactggcc ttgcacatta ctctcgcatt ccacagctgg ctggaggagt tatctttact     240
tcttctttgt gactgtggct gcatgaggcg cttagtatac tatcagctga tactatgttg     300
aaactgaatc acggtgcttg aaggtctgcg tgaagtggtt cattgggctg tgatattaac     360
cgcagcctgt ctagaactat gactagacgg agcgccaaga atggacgaca acaggaatac     420
tgcccagcta gccacagctg aatcctaaag aagtttgcca gccctcgtat tcctatcctg     480
catggacggc aacattgccc tgacgagcta aattaggccg cagcgctagt attagaatga     540
actacggtag caatgagggg aacgcccaca agccaattaa acgtcccttt cttgatatga     600
cgggcctagc cttaattacg gggtactgtg aggacgttgt gcctgctgca attgtctatc     660
cgtgccgacg gtgttgacag ccactagcca ttcagctcgc cacactttca accccacacc     720
tcaaagtaag acctaaactt attttggact tccttgcagc tactatgctg tcactgttat     780
```

-continued

```
ttgactggac atgacatgca gtatcatggc gccaataaag agagtatctc gagagtttca      840
ttgcatcgta ggaaaggctt gcattccggt gttgccggga aagggatcat tggtaatgcg      900
tagttgtttt gtctagctgt gatgccgggc tttgatggac ggaggacctg gagtgcagct      960
cttcatgcaa agcccgagat agactgattt gtaacatgtg tgatgcgtat cattcattat     1020
caatacgtct cgtggatatt taagaagggc gacagtcgtg tgaatatccg ctacttcaag     1080
ttcaaaacat cattcctacg aaaggaaaa ccacagcttc cgcttcaaag ccctagtcaa       1140
cactagttca tcttctgatt actttggttc acaatgcgga acaaccttct ttttccctc      1200
aatgccattg ctggcgctgt cgcgcatccg tccttccta tccataagag gcagtcggat      1260
ctcaacgcct tcattgaggc acagacaccc atcgccaaac agggcgtcct caataatatc     1320
ggcgctgatg gcaagcttgt tgagggggct gccgctggta tcgttgtagc ctccccatcc     1380
aagagtaatc ccgactgttc gtacaatcct accctcaaga ccgcatgata ttaccacaga     1440
gctaactata tatagacttc tacacctgga cgcgcgacgc tggcctcacc atggaagaag     1500
tgatagagca attcatcggg ggagatgcga ctctcgagtc cacaatccag aattatgttg     1560
actctcaagc gaacgagcag gcagtctcca acccatcagg cggcctgtcg gatggctcgg     1620
gtcttgctga acccaaattt tacgtcaata tctctcaatt caccgattct tggggccgac     1680
cccagcgcga cgggccagcc ttacgtgctt ccgctttgat cgcatatggc aactctctga     1740
tttccagcga caaacaatct gttgtcaaag ctaacatctg gccaattgtc cagaatgact     1800
tgtcttatgt gggtcaatac tggaaccaga ccgggtttga tctttgggaa gaggttcagg     1860
gcagctcctt cttcactgtt gctgtgcagc acaaagcctt ggtggagggc gatgcgtttg     1920
caaaggcact cggagaggaa tgccaggcat gctccgtggc gcctcaaatc ctctgccatc     1980
ttcaggactt ctggaatggg tctgctgttc tttctaactt accaaccaat gggcgcagtg     2040
gactggatac caactctctt tgggctcca ttcacacttt tgatccagcc gccgcttgtg      2100
atgatacaac attccagccc tgctcctctc gcgccctgtc gaaccataag cttgtggttg     2160
actctttccg gtcggtctac ggtatcaaca atggacgtgg agcaggaaag gccgcggcag     2220
tgggcccgta cgcagaggac acctatcagg gaggcaatcc atggttggta ctctgtctca     2280
tatccaaagc ttaaactaat gaatattagg tatcttacca ccctggtcgc tgcggaattg     2340
ctctacgacg ccttgtatca gtgggacaaa caaggtcaag tgaacgtcac tgaaacttcc     2400
cttcccttct tcaaggacct ctccagcaat gtcaccaccg atcctacgc caagtcttcc     2460
tcagcctatg agtcgcttac gagcgctgtc aagacctacg cagacggctt catctccgtt     2520
gtccaggagt atactcccga tggcggtgct ttggctgagc agtacagtcg ggaccagggc     2580
accccagttt cggcatccga tctgacttgg tcttatgcag ctttcttgag tgctgttgga     2640
cgacgaaacg gcactgtccc tgctagctgg ggctcttcca cggccaacgc agttccaagc     2700
caatgttcgg ggggtacagt ttctggaagt tacactaccc caactgttgg gtcgtggtag     2760
atgtactttc cagtgcgtgt agtctactct gacctcgtgt cacgattgtt gcttttgcct     2820
gtctaaatgc gaccgtgctg tgcatgtttg ttaaatactg tcattcatct ttgtttcaac     2880
aacaaagatt acatcaatta gtgctagcta gacaataact tttacagttg caacgttagt     2940
cctagtatta tacatctcac cggatcctct tcaaacttca cggggtaacc aaaagaaagt     3000
aacaagacta agcctattga tactgtggtt ctaatcttat tttagtttcc tgtacgtcca     3060
ctgcaatcaa actaagtata catactacat cct                                  3093
```

HIGH EXPRESSION SYSTEM OF PROTEINS

DETAILED DESCRIPTION OF THE INVENTION

1. Field of the Invention

The present invention relates to a homologous or heterologous gene expression system in which at least a part of a promoter region of a tyrosinase-encoding gene (melO) of *Aspergillus oryzae* is used as a promoter. More specifically, in the present invention, an expression mechanism of a tyrosinase-encoding gene of *Aspergillus oryzae* has been investigated, and it has been consequently found that this gene is expressed in large quantities in liquid medium for a long period of time. It relates to a construction of a system in which homologous or heterologous genes are expressed in large quantities with *Aspergillus oryzae* using this property, making possible the high production of useful proteins.

2. Description of the Related Art

The development of the genetic recombination technology in recent years has enabled useful human proteins to be produced with *Escherichia coli* or yeast. However, when genes derived from eucaryotes such as humans are expressed using *Escherichia coli* as a host, such problems have been pointed out that normal processing is not conducted and a sugar chain is not adhered. Further, when secretory production of heterologous proteins is conducted with yeast, sugar chain linkage is conducted, but there is a defect that the secretion amount thereof is very small. Accordingly, fungi having a high protein secretion ability have attracted considerable attention as a host of eucaryotic protein expression. Of these, *Aspergillus oryzae* has been long used in the brewing industry of sake and miso, and it has been therefore positively applied to the heterologous gene expression. An acid protease of *Mucor miehei* has been already industrially produced using *A. oryzae* as a host.

Since *Aspergillus oryzae* provides large amounts of amylase proteins such as α-amylase and glucoamylase, the promoters of these amylase genes are used for the production of heterologous proteins. The use of a gene promoter such as a protease or a 3-phosphoglycerate kinase has been studied. However, the expression amount thereof is far smaller than the expression amount of the promoters of amylase genes, especially the α-amylase gene. Accordingly, in order to highly express heterologous protein genes with *Aspergillus oryzae*, there is actually no way but to use the promoters of amylase genes. Problems that the Inveniton is to Solve.

The promoters of amylase genes, especially the promoter of α-amylase gene exhibits quite high expression even in submerged culture, and its usefulness in the heterologous protein production has been admitted (Japanese Patent Laid-Open No. 51067/1995), but there is a need to add an inducer such as starch or oligosaccharides to a medium. Further, when proteins producing glucose, such as glucoamylase and glycosidase, are expressed as heterologous proteins, glucose is produced in a large amount by the proteins expressed, so that a phenomenon of decreasing the production amount through glucose repression is observed. Accordingly, in order to widen a possibility of producing recombinant proteins with *Aspergillus oryzae*, it is required to study a promoter having a high expression ability in a control system different from the amylase system.

A glucoamylase that *Aspergillus oryzae* produces in solid-state culture is an important enzyme in the enzyme industry using a high sugar content. However, since glaB gene (Japanese Patent Laid-Open No. 84968/1998) which is its gene is little expressed in submerged culture, it cannot be mass-produced in submerged culture. Further, when recombinant proteins are produced using a high expression promoter, a large amount of glucose is formed by the recombinant proteins, so that the promoter of amylase genes does not allow the high production. The discovery of a promoter which shows a gene control system having a high expression ability, other than the amylase-type gene control system enables the production of glaB-type glucoamylase which was difficult so far in submerged culture.

In view of these circumstances, upon studying genes that can be highly expressed in submerged culture with *Aspergillus oryzae*, the present invention aims at high production of useful proteins such as glucoamylase using the promoter of high expression gene.

BRIEF DESCRIPTION OF THE DRAWINGS

FIG. 1 shows a plasmid for promoter analysis.

FIG. 2 shows the base sequence of melO gene promoter.

FIG. 3 shows base sequence 1 of the fusion gene of melO gene promoter and glaB translation region.

FIG. 4 shows the continuation of base sequence 1 in FIG. 3.

MEANS FOR SOLVING THE PROBLEMS

Figure 5A:
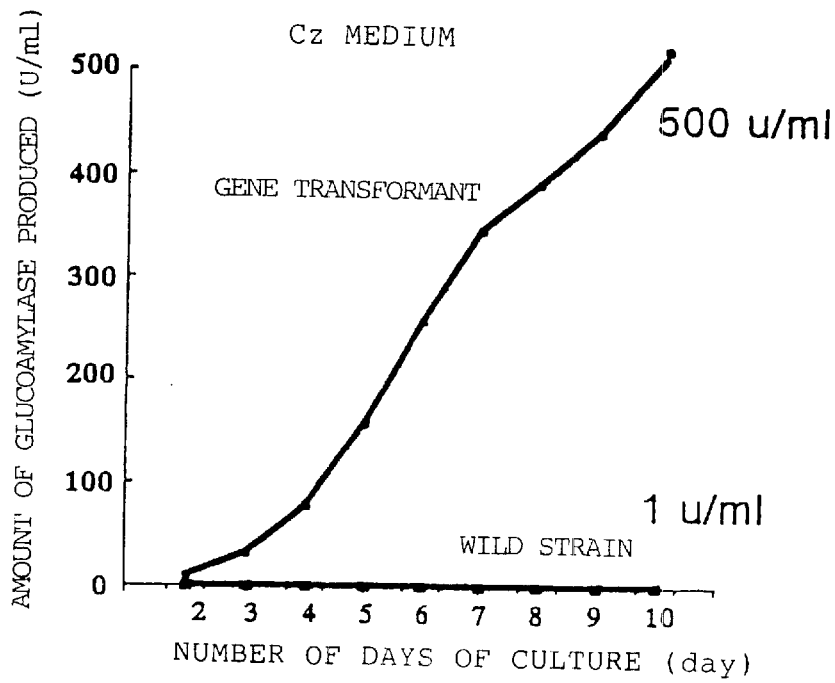
FIGS. 5A and 5B show the time course of glucoamylase production in CZ medium (FIG. 5A) and DPY medium (FIG. 5B).

In order to achieve the aim, the present inventors first studied expression abilities of various genes of *Aspergillus oryzae* using a promoter analysis system, and employed, with respect to the promoter analysis, a method in which a reporter gene is fused to a downstream region of a promoter to be studied and the activity of the reporter gene product is used as an index of the promoter expression. As a result of studying promoters of various genes, they have found an appropriate promoter. After further studies, they have succeeded in production of a high gene expression system, and have completed the present invention.

The present invention is described in detail below.

As the promoter analysis system for developing the high expression system according to the present invention, a promoter analysis plasmid pNGUS shown in FIG. 1 has been specifically used. This plasmid contains niaD gene (S. Unkles et al., Mol. Gen. Genet., 218, pp. 99–104, 1989) which is a transformation marker and uidA gene (R. A. Jefferson et al., Proc. Natl. Acad. Sci., pp. 8447–8451, 1986) encoding β-glucuronidase (GUS) of *Escherichia coli* which is a reporter gene. Various gene promoters to be studied or a part thereof were inserted in a upstream region (for example, SalI, PstI site) of the uidA gene of this plasmid. The resultant plasmid for promoter analysis was introduced into a niaD auxotroph (nitric acid assimilation ability-deficient strain, deficient in nitrate reductase: *Aspergillus oryzae* 1013-niaD, FERM P-17707) of *A. oryzae* (*Asperaillus oryzae* O-1013: this strain has been already deposited as FERM P-16528 in the International Patent Organism Depository, National Institute of Advanced Industrial Science and Technology, AIST Tsukuba Central 5, 1-1, Higashi 1-chome, Tsukuba-shi, Ibaraki-ken, 305–8566, Japan), and a transformant in which one copy of the introduction plasmid was introduced at niaD loci of a host chromosome was selected. The GUS activity of the transformants was measured and an index of a promoter activity was made.

As a result of studying promoters of various genes, a strong expression ability in submerged culture was observed in melO gene (Biochim. Biophys. Acta., 1261 (1), pp. 151–4, 1995), a tyrosinase-encoding gene of *Asperigillus oryzae*. This gene is isolated as a gene participating in a browning phenomenon in koji culture which is solid-state culture for making koji with *Aspergillus oryzae*. It has not been reported that this is strongly expressed in submerged culture. When a GUS gene was fused to the downstream region of this gene promoter, the expression ability in submerged culture was approximately the same as that of the promoter of α-amylase gene, amyB, or glucoamylase gene, glaA. The production of the recombinant protein with this gene promoter showed the same production amount in a glucose medium or a starch medium, and it became apparent that the protein productivity is not influenced by the carbon source in the medium. Moreover, it was identified that this gene increases the expression ability by prolonging the incubation term, and further that the higher expression is enabled by adjusting the incubation term.

The present inventors have therefore focussed on the promoter of the melO gene (its base sequence is shown in FIG. 2), and have newly constructed a fusion gene by linking a coding region of the glaB gene of *Aspergillus oryzae* to a downstream region of the melO gene promoter through the gene manipulation technology ordinarily used in the gene engineering. The base sequence of the resulting novel fusion gene is shown in Sequence Number 1 (and FIGS. 3 and 4). A region starting from position 1 and ending in position 1173 as shown in the base sequence of FIG. 3 is a melO promoter region, and a region starting from position 1174 and ending in position 3093 as shown in FIGS. 3 and 4 is a glaB translational region.

A glucoamylase was produced through submerged culture by introducing the new recombinant plasmid (including the sequence of Sequence Number 1) produced by linking the melO gene promoter to the coding region of glab gene as described above according to the usual method of the genetic recombination technology. This transformant was subjected to submerged culture for 10 days in a Czapek-Dox medium using glucose as a carbon source to produce 500 U/ml or more of a glaB-type glucoamylase. This showed the productivity which was more than twice as high as that in solid-state culture for making koji. Thus, the glucoamylase production which was higher than in solid-state culture was achieved by this culture method. Further, it was identified for the first time that in this culture, almost no protein other than the glucoamylase, a recombinant protein was produced in the medium and the recombinant protein having quite a high purity could easily be obtained. Such a useful new finding was obtained that a desired protein can be obtained at a high purity and in a high yield by using the melO promoter. This finding has led to the comletion of the present invention.

In other words, it has been clarified for the first time that homologous or heterologous genes can highly be expressed by using at least a part of 1173 base pairs of 5'-noncoding region of the melO gene as a promoter. According to the novel high expression system of the present invention, a variety of desired proteins can be freely obtained by linking structural genes encoding various proteins to the promoter by the usual method in the genetic recombination technology, introducing the expression plasmid containing the resulting fusion gene into *Aspergillus oryzae*, and incubating the thus-obtained transformant.

The protein expression system using the melO gene promoter is thus not only useful in the recombinant protein production of amylases such as glucoamylase but also applies widely to the expression of foreign genes. Further, according to the present protein expression system, a variety of genes are efficiently expressed. Still further, for example, the glab gene is inherently highly expressed in solid-state culture and shows a low productivity in submerged culture. However, the present system has enabled the glaB gene to be strongly expressed even in submerged culture. Moreover, such a remarkable effect is brough forth that recombinant proteins are highly produced without production of other proteins as by-products.

The present invention is illustrated by referring to the following Examples.

EXAMPLE 1

Study on Expression Ability of melO Gene

A melO gene promoter or a glaB gene promoter was inserted into an upstream region of the uidA gene of the plasmid for promoter analysis pNGUS, and introduced into *Aspergillus oryzae* (FERM P-17707). From the resulting transformants, the strain in which one copy of the plasmid was introduced was selected, and the GUS productivities in submerged culture and solid-state culture were compared. The results obtained are shown in Table 1 below.

TABLE 1

|  | Submerged culture | Solid-state culture |
| --- | --- | --- |
| glaB promoter | 93 | 8386 |
| melO promoter | 4040 | 48 |

GUS (U/mg-protein)

As is apparent from the results of Table 1 (GUS activities in submerged culture and solid-state culture), the glaB gene known to be strongly expressed in solid-state culture exhibited the high GUS productivity exceeding 8,000 U/mg-protein in solid-state culture. Meanwhile, in transformant of the melO promoter, almost no GUS activity was observed in solid-state culture, but the high productivity was shown in submerged culture. These results revealed that the melO gene was strongly expressed in submerged culture. Accordingly, the high production of heterologous proteins was enabled by using the melO promoter.

EXAMPLE 2

Production of glaB Glucoamylase

Figure 8:
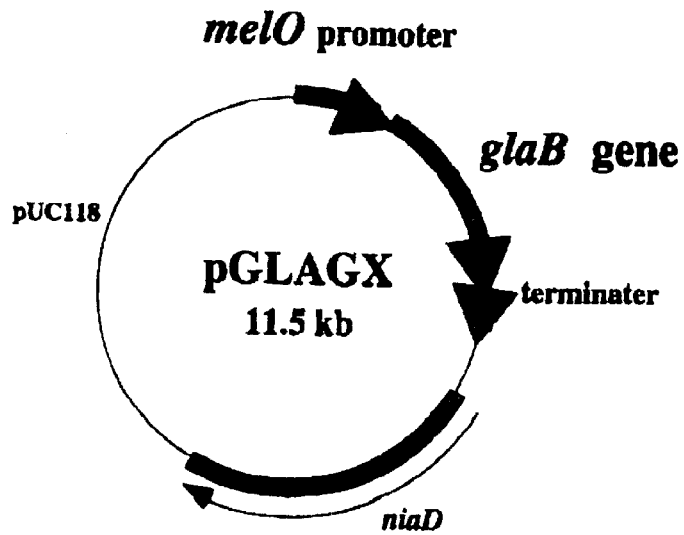
FIG. 8 shows *Aspergillus oryzae* expression plasmid pGLAGX.

A coding region of 1.9 kb glaB gene was linked to the downstream region of a 1.1 kb melO promoter by the combination PCR method of Higuchi et al. (PCR technology, Stockton Press, New York, pp 61–70) to prepare a fusion gene in which the initiation codon of the glaB gene was combined directly with the melO promoter. The base sequence thereof is shown in Sequence Number 1. The resulting fusion gene was introduced into vector pNIA2 to form *Aspergillus oryzae* expression plasmid pGLAGX (FIG. 8), and this was introduced into *Aspergillus oryzae* (FERM P-17707). The resultant transformant was named *Aspergillus oryzae* Mel-GLB and deposited in the National International Patent Organism Depository, National Institute of Advanced Industrial Science and Technology, AIST Tsukuba Central 5, 1-1, Higashi 1-chome, Tsukuba-shi, Ibaraki-ken, 305–8566, Japan under the Budapest Treaty on Jan. 26, 2002, and allotted No. FERM BP-7007.

Figure 5B:
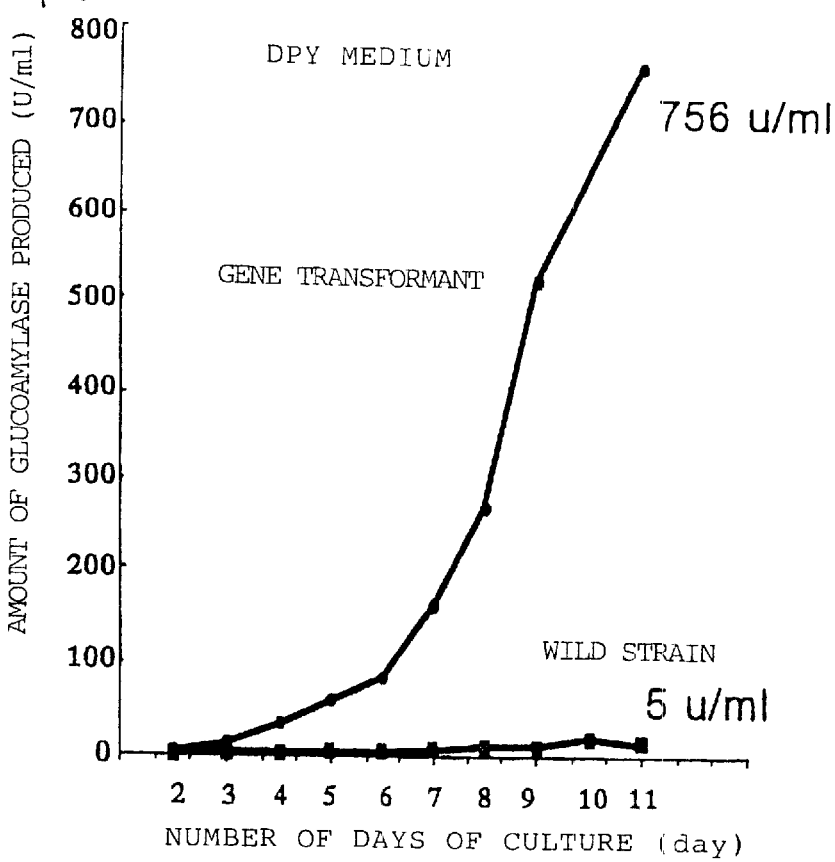

The resultant transformant was subjected to submerged culture at 30° C. in Czapek-Dox synthetic medium (Cz medium) and dextrin-peptone-yeast extract medium (DPY medium), and the glucoamylase activity in the culture supernatant was measured (FIG. 5). After 3 days of the culture, the glucoamylase was produced in the culture supernatant, and the high glucoamylase activity exceeding 500 U/ml was obtained after 10 days culture. In a nutritious medium such as DPY medium, the glucoamylase was produced at a high ratio of 756 U/ml equivalent to 1.4 mg/ml-broth as a protein. Further, even in a completely synthetic medium such as Cz medium, the glucoamylase was produced at a ratio of up to 500 U/ml. This was the high productivity which was approximately 100-fold higher than that in the submerged medium of an *A. oryzae* wild strain, and it was also the high productivity which was approximately more than twice as high as that in solid-state culture for making koji.

EXAMPLE 3

Purity of a Recombinant Protein

Figure 6:
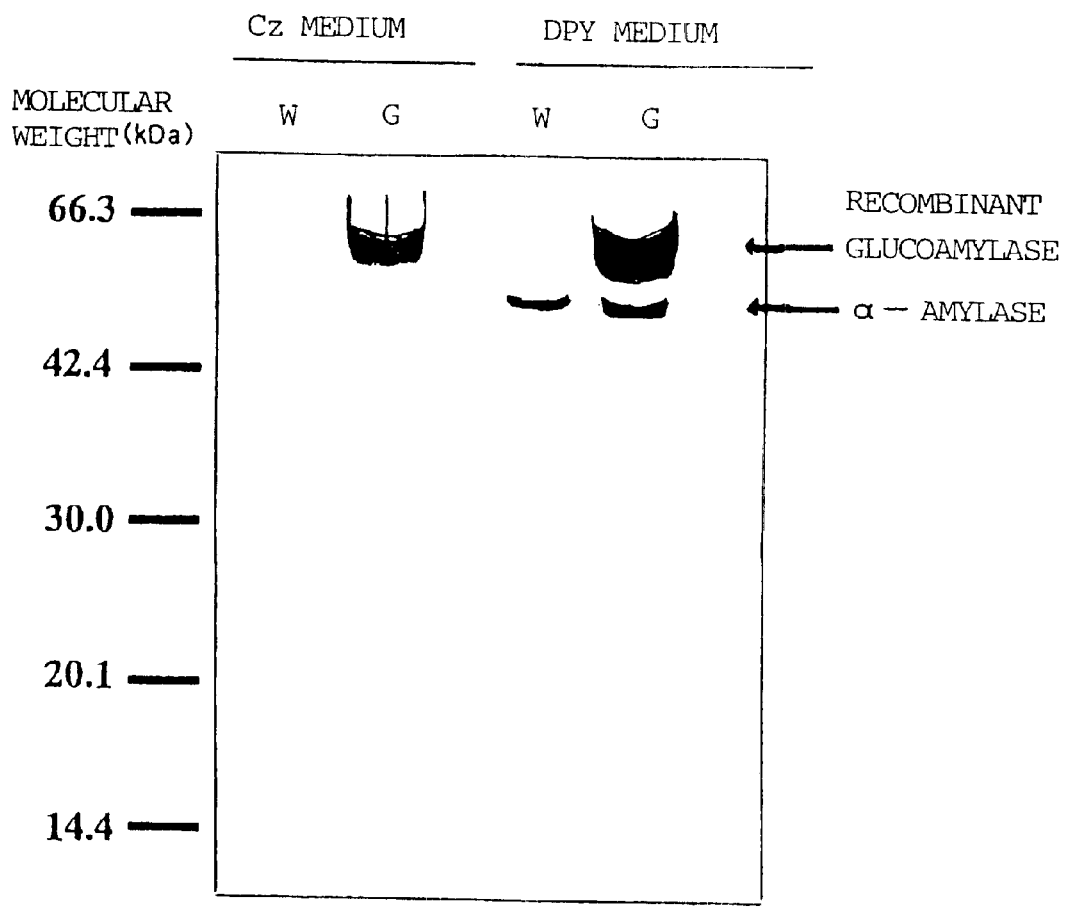
FIG. 6 is the SDS-PAGE pattern of a recombinant glucoamylase.

To examine the purity of the culture supernatant of the transformant shown in Example 2, the protein composition was analyzed through electrophoresis (FIG. 6). In DPY medium, signals of proteins other than the recombinant glucoamylase, such as α-amylase, were observed. However, in Cz synthetic medium, only the signal of the glucoamylase was detected. Thus, in the heterologous protein production using the melO promoter, it was proved not only that the production amount was large, but also that the purity of the protein produced was quite high.

EXAMPLE 4

High Production of Glucoamylase

Figure 7:
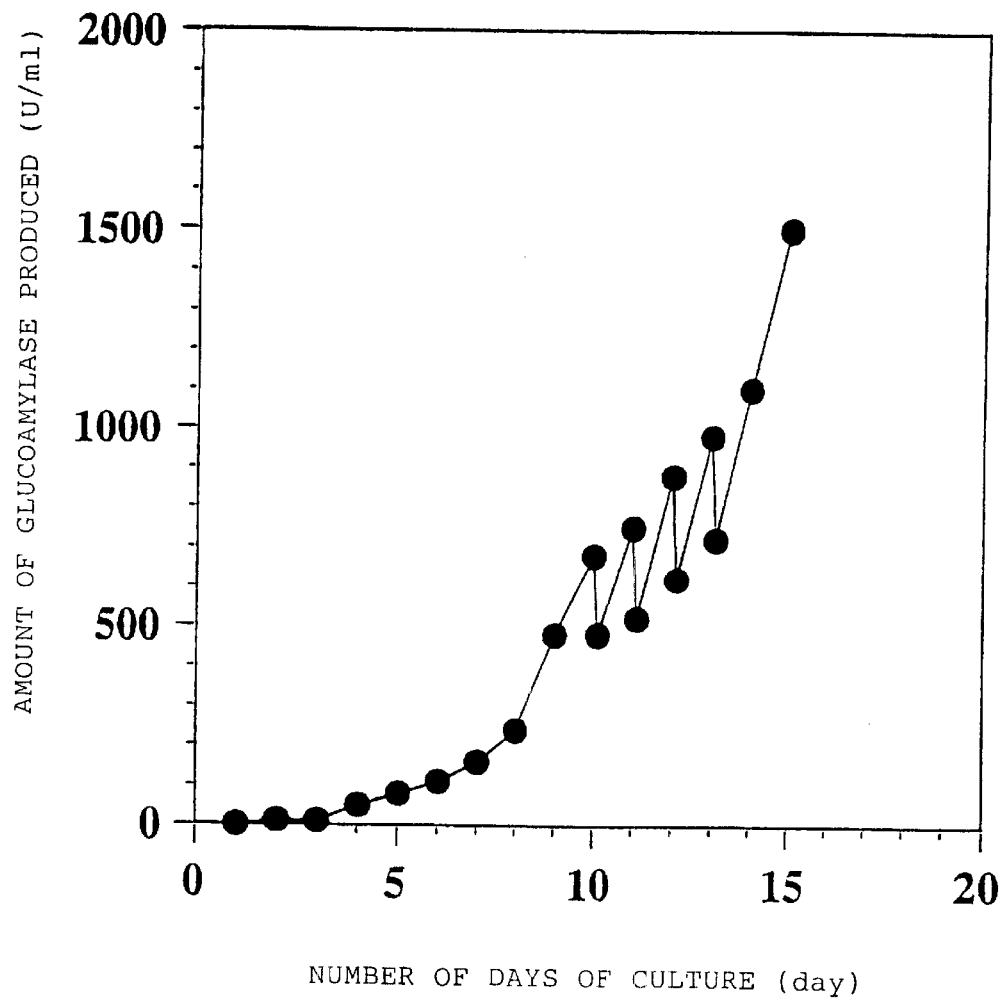
FIG. 7 shows the high production of glucoamylase at the terminal stage in submerged culture.

From Example 2, it was clarified that the melO gene was expressed after the cell growth reached to the steady period. Accordingly, the productivity of the glucoamylase was further increased by gradually adding the medium to the cells after the steady period (FIG. 7). Finally, 1,600 U/ml of the glucoamylase could be produced by fed-batch culture in which the medium was added to the cells after 10 days incubation in an amount of 15% each. Consequently, the productivity of the glucoamylase was further increased by 3.5 times in comparison with the batch culture. In this manner, it was identified that when the character of the melO gene expressed at the terminal stage of the culture is well utilized, still higher productivity of the heterologous protein can be achieved.

EFFECTS OF THE INVENTION

The present invention has, for the first time, enabled various genes to be effectively expressed by using a promoter region of melO gene, and can supply a desired protein by submerged culture at a high purity and in a high yield.

What is claimed is:

1. An isolated nucleic acid molecule represented by SEQ ID NO:1.

2. A recombinant vector into which the nucleic acid molecule according to claim 1 has been inserted.

3. A biologically pure culture of *Aspergillus oryzae* transformed with the recombinant vector according to claim 2.

4. The recombinant vector pGLAGX.

5. A biologically pure culture of *Aspergillus oryzae* Mel-GLB, FERM BP-7007.

6. A method for producing glucoamylase, comprising:

subjecting *Aspergillus oryzae* Mel-GLB, FERM BP-7007 to submerged culture in a liquid medium to produce glucoamylase; and recovering the expressed and produced glucoamylase from the resulting medium.

7. A method for producing a target protein, comprising:

subjecting *Aspergillus oryzae* to submerged culture in a liquid medium to produce the target protein; and recovering the expressed and produced target protein from the resulting medium, wherein the *Aspergillus oryzae* is a transformant which has been prepared by a procedure which comprises:

(a) preparing an isolated nucleic acid molecule comprising (1) a DNA fragment of SEQ ID NO:1 having promoter activity and (2) a DNA sequence fused to the DNA sequence of (1) and encoding the target protein, said DNA sequence of (2) having an initiation codon and a termination codon;

(b) preparing a recombinant vector comprising the isolated nucleic acid molecule of step (a); and (c) transforming *Aspergillus oryzae* with the recombinant vector of step (b).

8. The method according to claim 7, wherein said DNA fragment of (1) in step (a) comprises nucleotides 1 to 1173 of SEQ ID NO:1.

9. The method according to claim 8, wherein said target protein is glucoamylase (glaB) or β-glucuronidase (GUS).

10. The method according to claim 7, wherein said target protein is glucoamylase (glaB) or β-glucuronidase (GUS).

* * * * *